United States Patent [19]

Iwao et al.

[11] 4,255,446
[45] Mar. 10, 1981

[54] CYSTEINE DERIVATIVES

[75] Inventors: Jun-ichi Iwao, Takarazuka; Masayuki Oya, Ibaragi; Takehisa Chiba, Kyoto, all of Japan

[73] Assignee: Santen Pharmaceutical Co. Ltd., Osaka, Japan

[21] Appl. No.: 82,331

[22] Filed: Oct. 5, 1979

[30] Foreign Application Priority Data

Oct. 11, 1978 [JP] Japan ............................... 53-125539

[51] Int. Cl.³ ................. A61K 31/265; A61K 31/195; C07C 153/00; C07C 149/243
[52] U.S. Cl. ..................................... 424/301; 424/319; 260/455 R; 562/557
[58] Field of Search ............... 562/426, 557; 424/301, 424/319; 260/455 R

[56] References Cited

U.S. PATENT DOCUMENTS 4,053,651  10/1977  Ondetti et al. ..................... 562/426
4,137,420  1/1979   Fujita et al. ........................ 562/426

OTHER PUBLICATIONS

Wagner & Zook, "Synthetic Organic Chemistry", (1965), pp. 787, 788.

*Primary Examiner*—Alan Siegel
*Attorney, Agent, or Firm*—Frishauf, Holtz, Goodman & Woodward

[57] ABSTRACT

S-Substituted derivatives of N-(2-mercapto-2-methyl-propanoyl)-cysteine which have the formula

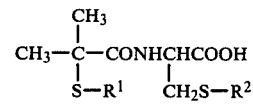

are useful as a medicine for suppressing liver disorders.

17 Claims, No Drawings

CYSTEINE DERIVATIVES

The present invention provides (1) a compound of the formula (I)

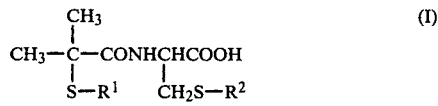

wherein $R^1$ and $R^2$ are lower alkanoyl, benzoyl, lower alkyl or lower alkyl substituted by carboxy; either $R^1$ or $R^2$ may be hydrogen; and a physiologically acceptable salt thereof, (2) a composition comprising a compound of the formula (I) and/or a physiologically acceptable salt thereof and a pharmaceutically acceptable excipient, (3) a method for suppressing liver disorders in a mammal comprising administering an effective dose of a compound of the formula (I) or a physiologically acceptable salt thereof, and (4) a process for producing a compound of the formula (I). Above mentioned lower alkanoyl and lower alkyl contain 1 to 6 carbon atoms.

Compounds of the formula (I) of the present invention are useful as a medicine for suppressing liver disorders due to their effect of removing free radicals.

Among cysteine derivatives of the formula (I), although compounds having hydrogen atoms in both $R^1$ and $R^2$ in the formula are well known as sputum resolvents, derivatives which have the substituted groups in $R^1$ and $R^2$ in the formula are novel compounds and their effects of suppressing liver disorders and their antirheumatic effects are newly found facts.

Methods for producing compounds of the formula (I) are generally classified into the following two methods (i) and (ii): Method (i):

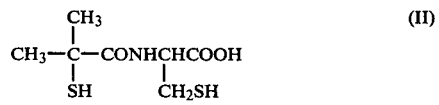

The compounds of the present invention can be obtained by reacting the compound of formula (II) and either carboxylic acids or halide of the formula, $R^3$-Y (III), (wherein $R^3$ is the same as for $R^1$ or $R^2$ in the formula (I) and the Y is hydroxyl or halogen) in such common methods as the Schotten-Baumann reaction where they are reacted in water, organic solvents, or mixed solvents of the former two, or the mixed acid anhydride method.

Method (ii):

The compounds of the present invention can be obtained by reacting a compound of the formula

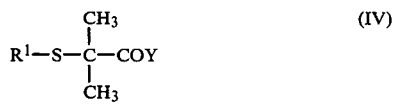

wherein $R^1$ or Y is the same as in the formula (I) or (III), respectively and cysteine in a similar way as in the case of method (i).

The compounds (I) obtained in the aforementioned methods (i) and (ii) are reacted with desired bases to form salts of the compounds (I) which can be approved as medicines can be obtained. Such bases are sodium hydroxide, sodium carbonate, potassium hydroxide, ammonium hydroxide, calcium carbonate, triethylamine, benzylamine, triethanolamine, N,N-dimethylethylenediamine, piperidine, N-ethylpiperidine, morpholine, N-ethylmorpholine, etc.

Since the compounds (I) of the present invention have one asymmetric carbon atom, there are stereoisomers. All of them are included in the category of the compounds of the present invention. The following examples illustrate the methods of producing the compounds (I), but are not intended to limit the invention.

EXAMPLE 1

S-Acetyl-N-(S-acetyl-2-mercapto-2-methylpropanoyl)-L-cysteine

N-(2-Mercapto-2-methylpropanoyl)-L-cysteine (11.2 g, 0.05 mol) is dissolved in 1 M potassium carbonate (250 ml) and acetyl chloride (15.7 g, 0.2 mol) is added dropwise while stirring under a nitrogen atmosphere at 0° C. After the addition, the mixture is stirred for 1 hour at room temperature and acidified with 6 N hydrochloric acid. The produced oil is extracted with ethyl acetate. The ethyl acetate layer is washed with water, dried and concentrated to dryness in vacuo to yield 10.7 g (69.6%) of S-acetyl-N-(S-acetyl-2-mercapto-2-methylpropanoyl)-L-cysteine.

m.p. 131°–132° C. (benzene). $[\alpha]_D^{27} -30.3°$ (c=1.3, methanol).

EXAMPLE 2

S-Benzoyl-N-(S-benzoyl-2-mercapto-2-methylpropanoyl)-L-cysteine

N-(2-Mercapto-2-methylpropanoyl)-L-cysteine (11.2 g, 0.05 mol) is dissolved in 1 M potassium carbonate (200 ml) and benzoyl chloride (21.1 g, 0.15 mol) is added slowly dropwise at 0° C. with stirring under a nitrogen atmosphere. After the addition, the mixture is stirred for 1 hour at room temperature and acidified with 6 N hydrochloric acid. The produced oil is extracted with ethyl acetate. The ethyl acetate layer is washed with water, dried and concentrated to dryness under reduced pressure to yield 9.7 g (45%) of S-benzoyl-N-(S-benzoyl-2-mercapro-2-methylpropanoyl)-L-cysteine.

m.p. 127.5°–128.5° C. (ethyl acetate). $[\alpha]_D^{28} -31.3°$ (c=1.4, methanol).

Analysis for $C_{21}H_{21}NO_5S_2$; Calculated: C, 58.45; H, 4.90; N, 3.25; Found: C, 58.28; H, 4.85; N, 3.24.

IR (nujol, $cm^{-1}$): 3260, 1730, 1659, 1622, 907, 894.

EXAMPLE 3

S-Pivaloyl-N-(S-pivaloyl-2-mercapto-2-methylpropanoyl)-L-cysteine

N-(2-Mercapto-2-methylpropanoyl)-L-cysteine (11.2 g, 0.05 mol) is dissolved in N sodium hydroxide (50 ml) and pivaloyl chloride (17.0 g, 0.13 mol) and aqueous N sodium hydroxide (150 ml) are added dropwise at 0° C. with stirring under a nitrogen atmosphere. After the addition, the mixture is stirred for 1 hour at room temperature and acidified with 6 N hydrochloric acid. The produced oil is extracted with ethyl acetate and the organic layer is washed with water, dried and concentrated to dryness under reduced pressure to yield 3.2 g (16.4%) of S-pivaloyl-N-(S-pivaloyl-2-mercapto-2-methylpropanoyl)-L-cysteine.

m.p. 140°–141° C. (ethyl acetate-petroleum benzine). $[\alpha]_D^{27} -30.0°$ (c=1.4, methanol).

Analysis for $C_{17}H_{29}NO_5S_2$; Calculated: C, 52.15; H, 7.47; N, 3,58; Found: C, 52.23; H, 7.55; N, 3.57.

IR (nujol, cm$^{-1}$): 3370, 1732, 1685, 1648, 941.

EXAMPLE 4

S-Pivaloyl-N-(2-mercapto-2-methylpropanoyl)-L-cysteine

N-(2-Mercapto-2-methylpropanoyl)-L-cysteine (11.2 g, 0.05 mol) is dissolved in N sodium hydroxide (50 ml) and then pivaloyl chloride (6.6 g, 0.055 mol) and N sodium hydroxide (60 ml) are added dropwise while stirring under a nitrogen atmosphere at 0° C. After the addition, the mixture is stirred for 1 hour at room temperature and acidified with 6 N hydrochloric acid. The produced oil is extracted with ethyl acetate. The organic layer is washed with water, dried and concentrated to dryness to yield 11.5 g (75.0%) S-pivaloyl-N-(2-mercapto-2-methylpropanoyl)-L-cysteine.

m.p. 115°-117° C. (benzene). $[\alpha]_D^{27} -25.7°$ (c=1.1, methanol).

Analysis for $C_{12}H_{21}NO_4S_2$; Calculated: C, 46.88; H, 6.88; N, 4.56; Found: C, 46.54; H, 6.93; N, 4.49.

IR (nujol cm$^{-1}$): 3335, 1743, 1687, 1625.

EXAMPLE 5

S-Carboxymethyl-N-(2-carboxymethylthio-2-methylpropanoyl)-L-cysteine

N-(2-Mercapto-2-methylpropanoyl)-L-cysteine (11.2 g, 0.05 mol) is dissolved in 1 M potassium carbonate and monochloroacetic acid (11.3 g, 0.12 mol) and potassium iodide (1.0 g) are added. The mixture is stirred overnight at room temperature under a nitrogen atmosphere and acidified with 6 N hydrochloric acid. Sodium chloride is added and the mixture is extracted with ethyl acetate. The organic layer is washed with saturated sodium chloride solution, dried and concentrated to dryness to yield 16.5 g (97.2%) of S-carboxymethyl-N-(2-carboxymethylthio-2-methylpropanoyl)-L-cysteine.

$[\alpha]_D^{25} -39.5°$ (c=2.0, methanol).

IR (neat, cm$^{-1}$): 1720, 1630, 1260, 1180.

EXAMPLE 6

S-Methyl-N-[2-methyl-2-(methylthio)propanoyl]-L-cysteine

N-(2-Mercapto-2-methylpropanoyl)-L-cysteine (11.2 g) is dissolved in 75 ml of 2 M potassium carbonate and methyl iodide (17.0 g) is added with stirring. The mixture is stirred for 1 hour at room temperature and then acidified with hydrochloric acid. The obtained crystals are separated by filtration and dried to yield 9.44 g (75.1%) of S-methyl-N-[2-methyl-2-(methylthio)-propanoyl]-L-cysteine.

m.p. 120.5°-121° C. (ethanol-n-hexane). $[\alpha]_D^{19} -19.3°$ (c=0.7, methanol).

IR (nujol, cm$^{-1}$): 3335, 1735, 1725, 1620.

NMR (CDCl$_3$, ppm): 1.53 (6H, s), 2.10 (3H, s), 2.15 (3H, s), 3.02 (2H, d, J=6 Hz), 4.55–4.90 (1H, m), 7.87 (1H, d, J=8H$_z$), 11.15 (1H, s).

EXAMPLE 7

N-[2-Methyl-2-(methylthio)propanoyl]-L-cysteine

L-Cysteine (7.1 g) is dissolved in 88 ml of 2 M potassium carbonate and 7.5 g of 2-methyl-2-(methylthio)-propanoyl chloride [b.p. 78° C. (37 mmHg)] is added dropwise while stirring under a nitrogen atmosphere at 0° C. After the addition, the mixture is stirred overnight at room temperature. The mixture is acidified with hydrochloric acid and the obtained crystals are separated by filtration and dried to yield 10.4 g (89.8%) of the titled compound.

m.p. 110.5°-112° C. (ethyl acetate). $[\alpha]_D^{19} +7.4°$ (c=1.1, methanol).

IR (nujol, cm$^{-1}$): 3350, 1730, 1620.

NMR (CDCl$_3$, ppm): 1.46 (1H, t, J=9H$_z$), 1.53 (6H, s), 2.10 (3H, s), 2.93–3.20 (2H, m), 4.66–4.95 (1H, m), 7.93 (1H, d, J=8 H$_z$), 10.40 (1H, s).

Suppressive effects of the compounds on liver disorders can be surveyed by administering drugs causative of liver disorders to animals and examining the suppressive effects of the compounds on the experimentally induced liver disorders. Among them, the drugs which induce experimental liver disorders are carbon tetrachloride, thioacetamide, bromobenzene, paracetamol, D-galactosamine, etc. It is particularly believed that, in liver disorders induced by carbon tetrachloride, cytochrome P-450 breaks carbon-chlorine bond producing free radicals (CCl$_3$) of strong toxicity which bring about disorders combining with thiol groups of proteins of the liver cell membrane or promoting the lipid peroxidation reaction of the membrane [Biochem. Pharmacol., 21, 49 (1972); 25, 2163 (1976)].

In the present invention, in order to investigate suppressive effects on liver disorders, carbon tetrachloride was employed as a drug which brings about experimental liver disorders and the suppressive effects of the compounds of the present invention on liver disorders were examined using serum transaminase (s-GOT and s-GPT) as an indicator.

Compounds employed in the experiments are as follows:

Compound A: S-Acetyl-N-(S-acetyl-2-mercapto-2-methylpropanoyl)-L-cysteine

Compound B: S-Pivaloyl-N-(S-pivaloyl-2-mercapto-2-methylpropanoyl)-L-cysteine

Compound C: S-Benzoyl-N-(S-benzoyl-2-mercapto-2-methylpropanoyl)-L-cysteine

PHARMACOLOGICAL TESTS

Male Wistar-strain rats of 170–200 g body weight, consisting of 5 rats each in one group, were kept without food for 16 hours and then used for experiments. 100 mg of the comounds A to C were orally administered per 1 kg of body weight. 0.25 ml of carbon tetrachloride was intraperitoneally administered per 1 kg of body weight (5 ml per 1 kg of body weight as an olive oil solution) 30 minutes after the administration of each compound. To the control, 5 ml of olive oil was intraperitoneally administered per 1 kg of body weight. Serum transaminase was determined 24 hours after the administration of carbon tetrachloride.

TABLE

Effect of the compound are on serum transmainase

| | Serum transaminase | | | |
|---|---|---|---|---|
| | Serum GOT | | Serum GPT | |
| Compound | Karmen unit/ml | Ratio | Karmen unit/ml | Ratio |
| None (Control) | 10428 ± 3118 | (100) | 2025 ± 650 | (100) |
| Compound A | 6236 ± 234 | (59.8) | 1656 ± 423 | (80.9) |
| Compound B | 7320 ± 822 | (70.2) | 1825 ± 171 | (90.1) |
| Compound C | 5806 ± 1152 | (55.7) | 1445 ± 207 | (70.6) |

Each value represents the means ± S.D. for 5 rats.

As shown in the table, it was found that serum transaminase was suppressed by the administration of the compounds A to C.

As clear from the above pharmacological test, the compound (I) of the present invention are useful as a medicine for suppressing liver disorders and are also expected to be an antirheumatic. When used for antirheumatic purpose, the compounds can be combined with thiol compounds depending on the cases as generally used at present. The compounds of the present invention are effective when administered in either manner of oral or parenteral administration and can be prescribed in either form of medicinal compositions for oral or parenteral administration depending on the need.

For oral administration, they can be prescribed as tablets, capsules, granules, etc. and are prepared pharmaceutically by mixing the compounds with at least one of such excipients as lactose, starch, sucrose, etc. Further, in preparing these medicine forms, other additives than the aforementioned excipients, such as disintegrators and covering materials as well as lubricants (magnesium stearate, etc.) and binders (dextrin) can usually be employed.

Medicines to be parenterally administered can be either in the form of sterilized aqueous or non-aqueous isotonic solution. In these medicines isotonicity adjuvants, such as preservatives, solubilizers and stabilizers can be added.

Although contents of the compounds of the present invention in any composition can be appropriately changed, they should be fixed to produce a suitable dosage. Dosage varies depending on the desired therapeutic effects, administration routes, subjects to be administered, duration of treatment, etc. Generally, to achieve desired effects, it is desirable to orally administer 0.2-20 mg of dosage level of the compounds of the present invention per 1 kg of body weight of patients a day. In the case of grown-ups, this can be attained by administering united medicine forms containing 50-30 mg of the compounds of the invention 1-3 times a day.

The following examples illustrate the description of medicines containing the compounds of the present invention as an effective ingredient. It is to be understood that said examples are not intended to limit the invention.

| (a) Tablet form | |
|---|---|
| Compound B | 100 mg |
| lactose | 100 mg |
| crystalline cellulose | 40 mg |
| carboxymethyl cellulose | 7 mg |
| magnesium stearate | 3 mg |
| Total | 250 mg |
| (b) Granular form | |
| Compound A | 100 mg |
| polyvinylpyrrolidone | 25 mg |
| lactose | 305 mg |
| hydroxypropyl cellulose | 50 mg |
| talc | 10 mg |
| Total | 490 mg |
| (c) Powder form | |
| Compound C | 300 mg |
| lactose | 230 mg |
| starch | 440 mg |
| colloidal silica | 30 mg |
| Total | 1000 mg |
| (d) Capsul form | |
| Compound A | 50 mg |
| lactose | 82 mg |
| crystalline cellulose | 56 mg |
| coloidal silica | 2 mg |
| Total | 190 mg |
| (e) Injection form | |

1 to 100 mg of the compound A in the form of the sodium salt is contained in 1 ml of an aqueous solution of pH 5.0-7.0.

We claim:

1. A compound of the formula

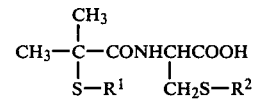

and a physiologically acceptable salt thereof within $R^1$ and $R^2$ are straight or branched $C_1$-$C_6$ alkanoyl, benzoyl, or $C_1$-$C_6$ alkyl substituted by carboxy and wherein $R^1$ and $R^2$ are the same.

2. The compound of claim 1, wherein $R^1$ and $R^2$ are acetyl, pivaloyl, benzoyl or carboxymethyl.

3. S-Acetyl-N-(S-acetyl-2-mercapto-2-methylpropanoyl)-L-cysteine.

4. S-Benzoyl-N-(S-benzoyl-2-mercapto-2-methylpropanoyl)-L-cysteine.

5. S-Pivaloyl-N-(S-pivaloyl-2-mercapto-2-methylpropanoyl)-L-cysteine.

6. S-Carboxymethyl-N-(2-carboxymethylthio-2-methyl-propanoyl)-L-cysteine.

7. A method for suppressing liver disorder in a mammal suffering from a liver disorder comprising administering an amount effective to suppress said liver disorder of a compound of the formula

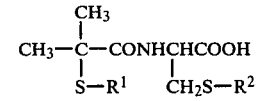

and a physiologically acceptable salt thereof wherein $R^1$ and $R^2$ are straight or branched $C_1$-$C_6$ alkanoyl, benzoyl, $C_1$-$C_6$ alkyl or $C_1$-$C_6$ alkyl substituted by carboxy; either $R^1$ or $R^2$ may be hydrogen.

8. The method of claim 7, wherein $R^1$ and $R^2$ are acetyl, pivaloyl, benzoyl, methyl or carboxymethyl.

9. The method of claim 7 or claim 8, wherein either $R^1$ or $R^2$ is hydrogen.

10. The method of claim 7, wherein said compound is S-acetyl-N-(S-acetyl-2-mercapto-2-methylpropanoyl)-L-cysteine.

11. The method of claim 7, wherein said compound is S-benzoyl-N-(S-benzoyl-2-mercapto-2-methyl-propanoyl)-L-cysteine.

12. The method of claim 7, wherein said compound is S-pivaloyl-N-(S-pivaloyl-2-mercapto-2-methyl-propanoyl)-L-cysteine.

13. The method of claim 7, wherein said compound is N-(2-mercapto-2-methylpropanoyl)-S-pivaloyl-L-cysteine.

14. The method of claim 7, wherein said compound is S-methyl-N-(2methyl-2-(methylthio)propanoyl)-L-cysteine.

15. The method of claim 7, wherein said compound is N-(2-methyl-2-(methylthio)propanoyl)-L-cysteine.

16. The method of claim 7, wherein said compound is S-carboxymethyl-N-(2-carboxymethylthio-2-methyl-propanoyl)-L-cysteine.

17. A medicinal composition for suppressing liver disorder in mammals comprising a pharmaceutically acceptable excipient and an amount sufficient to suppress the liver disorder of a compound of the formula

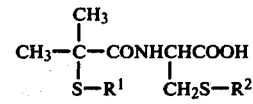

and a physiologically acceptable salt thereof wherein $R^1$ and $R^2$ are straight or branched $C_1$–$C_6$ alkanoyl, benzoyl, or $C_1$–$C_6$ alkyl substituted by carboxy; and wherein $R^1$ and $R^2$ are the same.

* * * * *

UNITED STATES PATENT AND TRADEMARK OFFICE
CERTIFICATE OF CORRECTION

PATENT NO. : 4,255,446
DATED : March 10, 1981
INVENTOR(S) : Jun-ichi IWAO et al

It is certified that error appears in the above—identified patent and that said Letters Patent is hereby corrected as shown below:

Column 4, line 46: change "comounds" to --compounds--.

Column 5, line 41: replace "50-30" with --50-300--.

Column 6, line 3: change "coloidal" to --colloidal--.

Signed and Sealed this

Twenty-ninth Day of December 1981

[SEAL]

Attest:

GERALD J. MOSSINGHOFF

Attesting Officer

Commissioner of Patents and Trademarks